United States Patent [19]

Kaufmann et al.

[11] 4,215,057
[45] Jul. 29, 1980

[54] PROCESS FOR THE PRODUCTION OF SUBSTITUTED FURANS

[75] Inventors: Rudolf Kaufmann, Burghausen; Herman Bräunling, Munich; Norman Häberle, Munich; Reinhard Müller, Munich, all of Fed. Rep. of Germany

[73] Assignee: Consortium für Elektrochemische Industrie GmbH, Munich, Fed. Rep. of Germany

[21] Appl. No.: 963,645

[22] Filed: Nov. 24, 1978

[30] Foreign Application Priority Data

May 1, 1978 [DE] Fed. Rep. of Germany ....... 2800502

[51] Int. Cl.² .................. C07D 307/46; C07D 307/68
[52] U.S. Cl. ............................... 260/347.5; 260/347.8
[58] Field of Search ........................... 260/347.5, 347.8

[56] References Cited

U.S. PATENT DOCUMENTS 4,025,537   5/1977   Kretchmer et al. .............. 260/347.5

FOREIGN PATENT DOCUMENTS 2006472   8/1970   Fed. Rep. of Germany.

OTHER PUBLICATIONS

Bisagni et al., Bull. Soc. Chim. France, (8) (1967), pp. 2796–2800.
Valenta et al., Coll. Czech. Chem. Comm., vol. 31, No. 6 (1966), pp. 2413 and 2414.
Elderfield, Heterocyclic Compounds, vol. 1, J. Wiley, New York (1950), pp. 132–134.
Scott et al., Journal of the American Chemical Society, vol. 54 (1932), pp. 2549–2556.
Bisagni et al., Bull. Soc. Chim. France, 1971 (II), pp. 4041–4047.

*Primary Examiner*—Richard Raymond
*Attorney, Agent, or Firm*—Allison C. Collard; Thomas M. Galgano

[57] ABSTRACT

A process for the production of substituted furans of the general formula

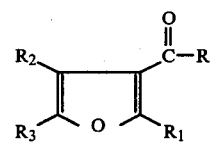

wherein R is a member of the group consisting of alkoxy radicals having from 1–6 C-atoms, a substituted aryloxy radical, an unsubstituted aryloxy radical and an alkyl radical, $R_1$ is a alkyl or aryl radical with 1–6 C-atoms, preferably methyl, $R_2$ and/or $R_3$ is an alkyl radical with 1–6 C-atoms or hydrogen by reacting a β-dicarbonyl compound with an α-chlorocarbonyl compound in the presence of a compound capable of combining with the hydrochloric acid formed, at temperatures between 30° and 100° C., the reaction being carried out at pH values between 2 and 7, preferably between 3.5 and 6, with the addition of equimolar amounts of an alkaline earth carbonate.

6 Claims, No Drawings

PROCESS FOR THE PRODUCTION OF SUBSTITUTED FURANS

The present invention relates to the production of substituted furans.

It is known from the literature to react β-dicarbonyl compounds with α-halogencarbonyl compounds; the process is called Feist-Benary-Synthesis. (See R. Elderfield, Th. Dodd in "Heterocyclic Compounds", Vol. 1, Editor, R. Elderfield, J. Wiley, New York, 1950, p. 132 ff). When working in the presence of ammonia, mixtures of furan and pyrrole derivatives are obtained. Scott and Johnson, J.A.C.S., 54, 2549 (1932) obtained a product free of pyrrole in yields of 50–60% in the presence of equimolar amounts of pyridine.

In the presence of other basic compounds, too, only low yields referring to β-dicarbonyl compounds were obtained, e.g., in the presence of sodium carbonate, sodium acetate, triethylamine, sodium hydroxide, potassium hydroxide; even in the presence of ice, only yields of 51% were obtained (see E. Bisagni et al., Bull. Soc. Chim. France, 1971 (II)p. 4041 ff.).

According to the German Offenlegungsschrift (application laid open for inspection) 20 06 472 it is even necessary to use 3 mol pyridine for each mol diketone. Indications of yields are not given in this publication. The low yields are a disadvantage of all known processes. Furthermore, it is a shortcoming of some processes, that large amounts of pyridine have to be used, which is expensive on the one hand, and makes further processing of the reaction products difficult.

It is an object of the present invention to provide a process for the production of substituted furans which leads to better yields and which does not require the use of larger amounts of pyridine.

Other objects and advantages of the invention will become apparent from the following specification.

According to the invention substituted furans are obtained having the general formula

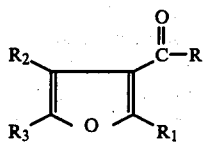

wherein R is a member of the group consisting of alkoxy radicals having from 1-6 C-atoms, preferably methoxy or ethoxy, a substituted aryloxy radical, an unsubstituted aryloxy radical and an alkyl radical, preferably methyl, $R_1$ is an alkyl or aryl radical with 1-6 C-atoms, preferably methyl, $R_2$ and/or $R_3$ is an alkyl radical with 1-6 C-atoms or hydrogen, preferably hydrogen, by reacting a β-dicarbonyl compound with a α-chlorocarbonyl compound in the presence of a compound capable of combining with the hydrochloric acid formed, at temperatures between 30° and 100° C., the reaction being carried out at pH values between 2 and 7, preferably between 3.5 and 6, with the addition of equimolar amounts of an alkaline earth carbonate, preferably with a particle size below 5 mm.

A suitable alkaline earth carbonate is ground dolomite, which is prepared in a special manner. For speeding up the reaction, it has proven advantageous to add up to 20 mol% of a substituted or unsubstituted mononitrogen compound, calculated on the β-dicarbonyl compound. The addition of 0.5–5 mol% pyridine, calculated on the dicarbonyl compound, is economical.

Surprisingly, the process according to the invention does not only improve further work-up of the reaction mixtures, but also leads to considerably better yields. It is possible to obtain up to 80 mol% of the desired product, calculated on the β-dicarbonyl compound used.

As mentioned above, the process according to the invention is carried out by reacting β-dicarbonyl compounds with α-chlorocarbonyl compounds. Suitable β-dicarbonyl compounds are: β-carbonyl ester, e.g., acetoacetic acid methyl-,ethyl-,-propyl-, and -phenyl ester, γ-chloroacetic ester, or β-diketones, e.g., acetyl acetone, heptanedione-3,5, and 1,3-propanedione-1,3.

Suitable α-chlorocarbonyls are, for instance, α-chloraldehydes, such as α-chloracetaldehyde, α-chloropropionaldehyde, α-chlorobutyraldehyde, and also α-chloroketones, e.g., α-chloroacetone, and 2-chlorobutanone-3.

As substituted or unsubstituted monoheterocyclic aromatic mononitrogen compounds pyridine is preferred, but others may also be used, e.g., picolines, lutidines or nicotinic acid.

In the reaction according to the invention, for preparing substituted furans, the β-dicarbonyl compounds may be used as such or dissolved in neutral organic solvents. However, no solvent is necessary for carrying out the process. As to the α-chlorocarbonyl compound, this may likewise be used as such, or an aqueous, preferably concentrated aqueous solution, may be used. The reactants are heated to the required reaction temperature of 30°–100° C., preferably 60°–80° C.

As basic compounds, alkaline earth carbonates are used according to the invention. The particle size is not particularly important; ground carbonates having a particle size below 5 mm are suitable. Especially good results were obtained with sizes between 1 and 200 μm, especially 55 μm. The alkaline earth carbonate is added in stoichiometrically required amounts.

Examples for the alkaline earth carbonates are calcium carbonate, both in precipitated and natural form, such as lime stone and chalk. Magnesium carbonate can likewise be used, for instance, in the form of dolomite; it proved to be especially satisfactory. For speeding up the reaction, it is advantageous to add up to 20 mol% of substituted or non-substituted monoheterocyclic aromatic mononitrogen compounds; pyridine is exceptionally well suited as a catalyst in quantities between 0.5 and 5 mol% calculated on the β-dicarbonyl compounds used.

It is one of the advantages of the invention that the addition of solvents and the use of aqueous solutions of the basic compounds can be dispensed with. This results in a considerable reduction of the volume of reaction products which is an improvement as compared to known methods. The alkaline earth halides, formed from the respective carbonates in the course of the reaction, are well soluble in water and can be easily separated or washed out with the aqueous phase after the reaction is completed.

The total reaction comprises substantially two steps: a condensation reaction and a ring closure reaction. The optimum pH value for the condensation reaction is 2–7, especially 3.5–6.0. The end of this reaction can be observed when the formation of carbon dioxide stops. The following operation requires adjustment depending on the α-chlorocarbonyl compounds used (α-chloraldehyde or -ketone). When α-chloraldehyde is reacted with β-dicarbonyl compounds, the ring closure can be improved by decreasing the pH value, while in the reaction with α-chloroketones it is preferably carried out with the same pH value as the condensation step. The ring closure follows the condensation in the same vessel and at the same temperature.

After completion of the reaction, the aqueous phase is separated and further work-up is carried out in a conventional manner, e.g., by vacuum distillation.

In the following, the process of the invention will be more fully described in a number of examples, but it should be understood that these are given by way of illustration and not of limitation.

EXAMPLE 1

Preparation of 2-methylfuran-3-carboxylic acid methyl ester.

58.055 kg (500 mol) acetacetic acid methyl ester are introduced into a vessel with a stirrer and 22.5 kg (487.5 Val) of ground dolomite having a grain size of 30 μm are mixed therewith. Then 0.988 kg (12.5 mol=2.5 mol%) pyridine are added thereto and the mixture is heated to 70° C., whereupon 87.2 kg (500 mol) 45% aqueous chloracetaldehyde solution are metered in within one hour. The temperature in the reaction is maintained at 70° C. by slight cooling. About 4 hours after the onset of the reaction, light heating is required; after 6-7 hours, heating to 75°-80° C. is performed, and thereafter heating is discontinued and stirring is continued for some time at falling temperatures. To the reaction mixture cooled to room temperature, concentrated hydrochloric acid is added in portions in order to decompose excessive dolomite. After separation of phases the aqueous bottom layer is removed and the organic layer washed with 76 liters of water. For better phase separation, about 2 kg. salt are added. The organic phase, which is now the bottom phase, is separated and distilled under reduced pressure. The yield in 2-methyl-3-carboxylic acid methyl ester amounts to 53.6 kg=76.6% of the theoretical amount.

EXAMPLE 2

Preparation of 2-methyl-3-acetylfuran.

To 100.12 g acetylacetone, 44 g dolomite powder and 4 ml pyridine (5 mol%) are added as described in example 1, whereafter 174.4 g 45% aqueous chloracetaldehyde solution is added, with stirring. Stirring is continued at 70° C. for 4.5 hours, and then another hour at 75° C. The $CO_2$-volume generated is 10.8 liter at room temperature. Workup occurs as in example 1. A fraction is collected at temperatures from 59°-61° C. at 11 torr; it amounts to 93.56 corresponding to 75.5% of the theoretical.

NMR (Nuclear Mass Resonance)-spectrum ($CDCl_3$,TMS as int state): 2,38,S,3H; 2,54,S,3H; 6,75,d,J=2,1 Hz,1H 7.38,d,J=2,1 Hz,1H.

In summary, it may be stated that for the production of furan derivatives by reaction of β-dicarbonyl compounds with α-chlorocarbonyl compounds up to now, it was only possible to obtain the desired compounds in low yields and that an improvement of these yields required the use of at least equimolar amounts of pyridine. This, in turn, makes the further processing or work-up of the reaction mixture cumbersome and the waste water purification difficult by the large amount of pyridine. Contrary thereto, the method of the invention uses stoichiometric amounts of alkaline earth metal carbonate, if necessary with at most 20 mol% of a mononitrogen compound, such as pyridine as acid binding compounds in the reaction. By the process according to the invention it is therefore possible to considerably increase the yields of the desired products and to avoid the use of pyridine either completely, or to a large extent.

While only several examples and embodiments of the present invention have been described, it will be obvious to those persons of ordinary skill in the art, that many changes and modifications may be made thereunto, without departing from the spirit and scope of the invention.

What is claimed is:

1. A process for the production of substituted furans of the general formula

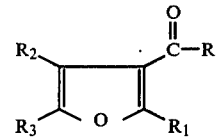

wherein R is a member of the group consisting of alkoxy radicals with 1-6 C-atoms, a substituted aryloxy radical, an unsubstituted aryloxy radical, and an alkyl radical, $R_1$ is an alkyl or aryl radical with 1-6 C-atoms, $R_2$ and $R_3$ respectively, or both, represent an alkyl radical with 1-6 C-atoms, and hydrogen, by reacting a β-dicarbonyl compound with an α-chlorocarbonyl compound in the presence of a compound capable of combining with hydrochloric acid formed, the process being characterized in that the reaction is carried out in water at pH values between 2 and 7 with addition of equimolar amounts of an alkaline earth carbonate and wherein to the reaction mixture 0.1-20 mols % are added of a substituted or unsubstituted mononitrogen compound calculated on the β-dicarbonyl compound.

2. The process according to claim 1, wherein R stands for a methoxy or ethoxy radical.

3. The process according to claim 1, wherein the alkyl radical is methyl.

4. The process according to claim 1, wherein the reaction is carried out at a pH value of 3.5-6.

5. The process according to claim 1, wherein 0.5-5 mol% of pyridine are added to the reaction mixture.

6. The process according to claim 1 wherein ground dolomite with a particle size below 5 mm is added as the alkaline earth carbonate.

* * * * *

UNITED STATES PATENT AND TRADEMARK OFFICE
CERTIFICATE OF CORRECTION

PATENT NO. : 4,215,057

DATED : JULY 29, 1980

INVENTOR(S) : RUDOLF KAUFMANN ET AL

It is certified that error appears in the above—identified patent and that said Letters Patent is hereby corrected as shown below:

Cover Page, [75] Inventors, change "Herman Bräunling" to --Hermann Bräunling--; [30] Foreign Application Priority Data, change "May 1, 1978" to --January 5, 1978--; and change "2800502" to --2800505--. Column 1, line 56, change "a" (second occurrence) to --an--.

Signed and Sealed this

Twenty-eighth Day of October 1980

[SEAL]

Attest:

SIDNEY A. DIAMOND

Attesting Officer

Commissioner of Patents and Trademarks